United States Patent
Kong et al.

(10) Patent No.: US 7,848,797 B2
(45) Date of Patent: Dec. 7, 2010

(54) MOTOR UNIT NUMBER ESTIMATION (MUNE) FOR THE ASSESSMENT OF NEUROMUSCULAR FUNCTION

(75) Inventors: Xuan Kong, Acton, MA (US); Zhixiu Han, Acton, MA (US); Shai N. Gozani, Brookline, MA (US)

(73) Assignee: NeuroMetrix, Inc., Waltham, MA (US)

( * ) Notice: Subject to any disclaimer, the term of this patent is extended or adjusted under 35 U.S.C. 154(b) by 0 days.

(21) Appl. No.: 11/893,737

(22) Filed: Aug. 17, 2007

(65) Prior Publication Data

US 2008/0051673 A1   Feb. 28, 2008

Related U.S. Application Data

(60) Provisional application No. 60/838,356, filed on Aug. 17, 2006.

(51) Int. Cl.
*A61B 5/04* (2006.01)
*A61B 5/05* (2006.01)

(52) U.S. Cl. .................. 600/546; 600/544; 600/545; 600/547

(58) Field of Classification Search .......... 600/544–546
See application file for complete search history.

(56) References Cited

U.S. PATENT DOCUMENTS

| | | | | |
|---|---|---|---|---|
| 4,592,369 A | * | 6/1986 | Davis et al. | 600/546 |
| 4,611,284 A | * | 9/1986 | McGill et al. | 600/546 |
| 5,092,343 A | * | 3/1992 | Spitzer et al. | 600/515 |
| 5,505,208 A | * | 4/1996 | Toomim et al. | 600/546 |
| 5,524,632 A | * | 6/1996 | Stein et al. | 600/546 |
| 5,687,716 A | * | 11/1997 | Kaufmann et al. | 600/300 |
| 5,797,853 A | * | 8/1998 | Musha et al. | 600/544 |
| 5,884,626 A | * | 3/1999 | Kuroda et al. | 600/300 |
| 5,928,143 A | * | 7/1999 | McNaughton | 600/373 |
| 6,280,394 B1 | * | 8/2001 | Maloney et al. | 600/546 |
| 6,280,395 B1 | * | 8/2001 | Appel et al. | 600/546 |
| 6,379,313 B1 | * | 4/2002 | Gozani et al. | 600/554 |
| 6,466,817 B1 | * | 10/2002 | Kaula et al. | 600/546 |
| 6,532,383 B2 | * | 3/2003 | Maloney et al. | 600/546 |
| 7,177,677 B2 | * | 2/2007 | Kaula et al. | 600/546 |
| 7,187,968 B2 | * | 3/2007 | Wolf et al. | 600/544 |
| 7,221,975 B2 | * | 5/2007 | Lindstrom | 600/509 |

(Continued)

OTHER PUBLICATIONS

Catherine Lomen-Hoerth, MD, PhD, and Richard K. Olney, MD, "Comparison of Multiple Point and Statistical Motor Unit Number Estimation", Muscle and Nerve, Oct. 2000, pp. 1525-1533.*

(Continued)

*Primary Examiner*—Max Hindenburg
*Assistant Examiner*—Sean P Dougherty
(74) *Attorney, Agent, or Firm*—Pandiscio & Pandiscio

(57) ABSTRACT

A method for the assessment of neuromuscular function by motor unit number estimation, comprising: (i) determining and controlling stimulation and data acquisition process via pre-configured electrode array so as to acquire stable and less uncertainty MU responses; (ii) pre-processing acquired MUs responses so as to attenuate noise, determine MUs activity region, and improve processing speed and accuracy; (iii) minimizing alternation effects by globally searching and comparing SMUPs; (iv) eliminating alternation effects by identifying alternating MUs directly; and (v) computing and reporting MUNE results, as well as the statistical description of these MUN estimates to evaluate its robustness.

40 Claims, 11 Drawing Sheets

Motor units stimulus response curve

U.S. PATENT DOCUMENTS

| | | | |
|---|---|---|---|
| 2001/0025146 A1* | 9/2001 | Maloney et al. | 600/546 |
| 2001/0041846 A1* | 11/2001 | Appel et al. | 600/546 |
| 2003/0045808 A1* | 3/2003 | Kaula et al. | 600/546 |
| 2003/0191408 A1* | 10/2003 | Montgomery, Jr. | 600/544 |
| 2004/0225211 A1* | 11/2004 | Gozani et al. | 600/382 |
| 2006/0100540 A1* | 5/2006 | Gozani et al. | 600/554 |
| 2007/0031418 A1* | 2/2007 | Tabares et al. | 424/146.1 |
| 2007/0161919 A1* | 7/2007 | DiLorenzo | 600/544 |
| 2007/0179399 A1* | 8/2007 | Viertio-Oja et al. | 600/559 |
| 2007/0276281 A1* | 11/2007 | Sarkela | 600/546 |
| 2008/0108908 A1* | 5/2008 | Maddess et al. | 600/544 |

OTHER PUBLICATIONS

Richard K. Olney, MD, Eric C. Yuen, MD, and John W. Engstrom, MD "Statistical Motor Unit Number Estimation: Reproducibility and Sources of Error in Patients With Amyotrophic Lateral Sclerosis", Muscle and Nerve, Feb. 2000, pp. 193-197.*

Robert D. Henderson, FRACP, Robyn McClelland, PhD, and Jasper R. Daube, MD, "Effect of Changing Data Collection Parameters on Statistical Motor Unit Number Estimates", Muscle and Nerve, Mar. 2003, pp. 320-331.*

* cited by examiner

Top-level flow chart of methods in this invention

An illustration of deferment of decision allowing more MUNE solution candidates

Illustrations of decomposed single motor unit potentials with poor and good scores.

SMUP validation using self-check methods

MOTOR UNIT NUMBER ESTIMATION (MUNE) FOR THE ASSESSMENT OF NEUROMUSCULAR FUNCTION

REFERENCE TO PENDING PRIOR PATENT APPLICATION

This patent application claims benefit of pending prior U.S. Provisional Patent Application Ser. No. 60/838,356, filed Aug. 17, 2006 by Xuan Kong et al. for MOTOR UNIT NUMBER ESTIMATION AUTOMATION WITH GLOBAL OPTIMIZATION, which patent application is hereby incorporated herein by reference.

FIELD OF THE INVENTION

This invention relates to methods and apparatus for the assessment of neuromuscular function, and more particularly to methods and apparatus for the assessment of neuromuscular function by estimating motor unit number (MUN). Among other things, this invention uses global optimization and direct identification of possible alternation patterns to overcome the limitations of previous strategies for estimating MUN.

BACKGROUND OF THE INVENTION

The study of MUN provides information about the structure and organization of the human brainstem and spinal cord, and the innervations of muscles. Motor unit number estimation (MUNE) is performed in order to detect and evaluate muscle denervation disorders such as amyotrophic lateral sclerosis (ALS), spinal muscular atrophy (SMA), poliomyelitis and other types of peripheral neuropathy. This MUNE technology has proven to be a useful tool for qualified healthcare professionals to diagnose and assess common neuromuscular disorders. Serial MUNE (multiple measures of MU number over a period of time) has also proven to be valuable in determining the natural time-courses of peripheral neuropathy, and evaluating the effectiveness of intervention procedures.

1. The MUNE Concept

The body's muscles are controlled by motor neurons residing in the spinal cord and brainstem. Motor neurons carry control signals from the brain or spinal cord to muscles. Muscle fiber is the basic functional unit of a muscle, and each motor neuron may innervate one or more muscle fibers through its motor neuron axon. As shown in FIG. 1, motor neuron 1 innervates three muscle fibers 12, 13 and 14 through motor neuron axon 11. Motor neuron 2 innervates two muscle fibers 22 and 23 through motor neuron axon 21.

A motor neuron and all the muscle fibers it innervates are called a motor unit (MU). In FIG. 1, there is shown two MUs: MU1 (made up of motor neuron 1, axon 11 and muscle fibers 12, 13 and 14) and MU2 (made up of motor neuron 2, axon 21 and muscle fibers 22 and 23). A large MU may contain between 50 and 200 muscle fibers. A muscle group may consist of up to hundreds of MUs. An example of a muscle group is the thenar muscles controlling the movement of the thumb.

Neuromuscular diseases may cause muscle fibers to lose the innervation of axons (denervation). If muscle fibers 22 and 23 lose innervation, they are no longer able to contract voluntarily. As a result, the muscle group loses strength and MUN decreases.

Neuromuscular diseases may also cause axon 11 to innervate with muscle fibers 22 and 23 after axon 21 loses its innervation with the two muscle fibers. Although muscle strength may be maintained in this case, the MUN will be reduced. An accurate estimation of MUN will reveal the diseases.

When a motor neuron (e.g., motor neuron 2 in FIG. 1) is activated, an action potential (AP) propagates along the nerve axon (e.g., nerve axon 21 in FIG. 1) and terminal nerve branches (e.g., the terminal nerve branch 25 in FIG. 1) and arrives at the neuromuscular junction or end plate (e.g., end plate 26 in FIG. 1). At the arrival of an AP, the nerve terminals release acetylcholine, which depolarizes the muscle membrane and results in an end plate potential (EPP). When the EPP exceeds the muscle membrane threshold level, it produces a muscle fiber action potential (FAP). The electric field generated in the vicinity of the muscle fibers can be detected by a skin surface electrode located near this field. The combination of the muscle fiber action potentials from all of the muscle fibers of a single motor unit is the single motor unit potential (SMUP). As an example, and looking now at FIG. 1, when an AP 15 activates muscle fibers 12, 13 and 14, the summation of the muscle FAP forms the SMUP_1 16 for motor unit 1.

The electrical activity of multiple MUs of a muscle group can also be measured by the same electrode and is referred to as a compound muscle action potential (CMAP). When all muscle fibers in a muscle group are activated, the measured CMAP is called maximum CMAP. Therefore, the MUN of a muscle group is estimated by using the average size of the SMUPs divided into the maximum CMAP. As an example, and looking now at FIG. 2, SMUP_1, SMUP_2, . . . , and SMUP_N are all single motor unit potentials of a muscle group, and their summation generates the maximal CMAP, i.e., CMAP_max 34. It is not practical to measure every SMUP, but a subset of SMUPs is measurable. The average of the measured SMUP waveforms is considered as a representative SMUP (e.g., SMUP_rep 35 in FIG. 2). Using peak-to-base amplitude as the size of CMAP and SMUP (36 and 37 in FIG. 2), one can estimate the MUN of the muscle group by dividing the numerical value of waveform characteristics 37 into the numerical value of 36. An alternative to using waveform characteristics 37 is to determine the numerical value 38 for each SMUP and then average those numerical values 38 so as to provide an estimate of the representative SMUP size.

2. MUNE Study

Several methods have been developed to estimate MUN for the diagnosis and assessment of neuromuscular disorders. These existing MUNE methods include incremental stimulation (IS), multiple point stimulation (MPS), adapted MPS, F-wave, spike-triggered averaging (STA) and statistical methods. The methods essentially differ from one another in the way in which they acquire the subset of SMUPs. Each of the approaches has specific strengths and limitations.

The IS Method. The IS method estimates SMUP from motor units with a low axon activation threshold. Individual electrodes are first placed over the skin of the subject who is to be studied. The electrode locations are selected based on the operator's knowledge and anatomical landmarks of the subject. Therefore, the electrode size, location, and inter-electrode distance may vary from study to study. Stimulation with intensity just below the activation threshold of motor axons is first applied and null response (baseline) is recorded. The stimulation intensity is then gradually and manually increased until the first recognizable and repeatable muscle response is obtained, representing the activation of the first motor unit. The recorded response is considered the first SMUP. The stimulus intensity is then increased, and a response larger than the previous one is obtained. The difference between the two responses is considered to be the second SMUP, i.e., the net response of the second motor unit. This process is then repeated a number of times. Usually up to 10 discrete increments are obtained, with each increment assumed to represent the addition of one motor unit. The waveforms corresponding to the discrete increments form the subset of SMUP for MUNE.

A physiological phenomenon called alternation complicates utilization of the IS method for MUNE. The alternation phenomenon occurs because activation thresholds of nerve axons often overlap. FIG. 3 illustrates this phenomenon. More particularly, FIG. 3 depicts the probability of motor neuron axon activation as a function of the stimulus strength. It can be seen that motor units MU1 and MU2 have a large common range of activation threshold with varying probabilities. Now consider the following scenario: an initial recorded response is attributed to motor unit MU1, and a subsequent stimulus leads to a response different from the first one. The second response could be the result of both motor units MU1 and MU2, or it could be the result of motor unit MU2 alone. This second condition is sometimes referred to the alternation, as two distinct motor units alternate their activations. If the alternation is not recognized and the difference of the two responses is considered as the SMUP of MU2, the response of MU2 will be under-estimated. Consequently, the MUN will be over-estimated. Indeed, the IS method often results in over-estimating the MUN in comparison with other MUNE methods.

The IS method is carried out manually by an expert. Recognizing the potential pitfall of alternation, the expert often spends a significant amount of time to determine whether the changes observed in the most recent response are due to alternation or activation of a new motor unit. If alternation involves n motor units, a maximum of $(2^n-1)$ alternation waveform patterns exist. For n>2 (e.g., motor units 3, 4, and 5 in FIG. 3), determination of the alternation pattern can prove to be a challenge too great for any human operator. Even without the complication of alternation, it is possible that electronic and physiological noise could also be mistaken as new motor units.

Multi-Point Stimulation (MPS). To sidestep the complexity of sorting out motor unit alternation patterns, the multi-point stimulation (MPS) method was developed. With this approach, multiple stimulation sites along the nerve axon path are used. For each stimulation site, a stimulus with an intensity low enough to activate only one motor unit is used and the response is recorded as SMUP. The stimulating electrode is then moved slightly along the axon path and the process is repeated. Often the responses are thereafter manually examined, and only those responses with different morphology and amplitude are accepted. This is to ensure that distinct motor units are sampled. Because each SMUP is obtained with a different latency (i.e., with a different nerve impulse traveling time from stimulator to detector), the SMUPs should not be combined directly to obtain a representative SMUP for determining the size of average SMUP. Instead, the feature of individual SMUP (e.g., amplitude, negative peak area, etc.) has to be calculated first and then averaged with other individual SMUPs. However, the SMUP feature obtained using this approach is generally inferior to the feature obtained from the averaged SMUP. This is because the feature may not be additive (i.e., the amplitude of two SMUPs added together is smaller than the summation of the two SMUP amplitudes, unless the peaks are aligned perfectly in time). This phenomenon may lead to under-estimation of the MUN.

Adapted MPS. The adapted MPS method is a hybrid of the IS and MPS methods. It still utilizes multiple stimulation sites. However, the method attempts to elicit more than one SMUP until alternation becomes evident. Often this means that ~2-3 SMUPs can be obtained at each stimulation site. While this method reduces the number of stimulation sites, it still shares the limitation of the MPS method, i.e., that SMUPs evoked from different stimulation sites cannot be easily combined. Both the Adapted MPS and MPS approaches can only be applied to long, accessible nerves.

The F-Wave Approach. Another method using surface electrode stimulation is the F-Wave approach. With this approach, the electrode placement is similar to that in the IS method. F-wave is a late response of a muscle group. It is generated by antidromic ("backfiring") of motor neurons following stimulation of peripheral nerve axons. Only a small fraction (i.e., about 2-5%) of motor neurons will backfire for each stimulus, with the backfiring occurring on a randomized basis (i.e., different motor neurons will backfire even under identical stimulation conditions). After the maximum CMAP is acquired, its size is determined. A commonly-used size measure is peak-to-base amplitude (shown at 36 in FIG. 2), peak-to-peak amplitude (shown at 42 in FIG. 2), and area-under-the-peak (shown at 41 in FIG. 2). The stimulus intensity is adjusted to evoke a CMAP with a size of 10-50% of the maximum. At the reduced intensity, the axons are stimulated up to 300 times at the same stimulation location. F-waves with identical morphology and latency are considered as the same SMUP because the probability for multiple motor neurons to backfire together more than once to form the same morphology is much lower. For illustration, it is assumed that the backfiring probability for each motor neuron is $p=0.02$. Given that an F-wave morphology is observed, the probability of the same F-wave morphology being observed again is $p=0.02$ if the F-wave is from a single motor neuron. The probability becomes $p*p=0.0004$ if the F-wave is a result of two motor neurons' backfiring together. The F-Wave method does not involve the challenge of assessing alternation, but the identified SMUPs may have different latency. Therefore, combining them directly may not yield a representative SMUP. However, the key assumption that an F-wave is a single motor unit potential if it occurs more than once may not be valid, particularly in a diseased population. Some motor neurons are also more likely to backfire than others, making the observed SMUPs a biased sample of the total motor unit pool.

Spike-Triggered Averaging (STA). The STA method uses surface electrodes to record SMUPs either with voluntary muscle contraction by subjects or by applying electric stimulation. With the voluntary muscle contraction approach, a needle is inserted into muscle to detect the spike associated with a specific SMUP. The spike is then used as the trigger to synchronize the surface recordings in order to estimate the corresponding SMUP. The needle position is adjusted multiple times to probe different motor units. With the electric stimulation approach, a needle is inserted to deliver micro-stimulation to individual motor axons. While kept at the same insertion point, the needle electrode tip position is manually adjustable to activate different axons in the nerve bundle. The surface recorded responses are time-synchronized with stimulus onset and averaged to yield SMUP. Multiple SMUPs acquired with either approach are utilized in the same manner as with other methods to generate MUNE. One advantage of the STA technique is that it can reach proximal muscles, whose nerves are usually inaccessible by other methods.

However, this approach is invasive, causes greater discomfort to subjects than other methods, and requires skillful operators.

Statistical Methods. Statistical methods are fundamentally different from other MUNE methods. With these statistical methods, a series of CMAPs are recorded at fixed, sub-maximal stimulation intensities. Axons near threshold will be activated intermittently, resulting in small CMAP variations. The estimated size of individual SMUPs that are activated intermittently is calculated from the variance of the CMAP. The total MUNE is calculated by dividing the maximal CMAP size by the estimated SMUP size obtained at different intensities. This MUNE method evaluates motor unit size throughout the entire response range from threshold to supramaximal. It depends less on operator expertise and eliminates the issue of alternation, but requires a high number of stimuli.

Thus there is a need for a new approach for estimating motor unit number (MUN) which addresses the problems of the prior art.

SUMMARY OF THE INVENTION

The present invention provides a novel approach to address the limitations of the IS method while maintaining its advantages, such as low stimulation count, single stimulation site, non-invasiveness, and minimum stimulus intensity for maximum patient comfort. Through computerized waveform analysis, alternations can be identified effectively. Automation in stimulus control and waveform processing ensures accurate and efficient MUNE for various clinical applications. Two different approaches to address the issue of alternation are presented. The first approach utilizes global optimization. The second approach involves direct identification of possible alternation patterns. Details of each of these approaches will hereinafter be discussed in further detail.

More particularly, the present invention provides methods and apparatus for estimating motor unit numbers in a muscle group. The method for MUNE involves differentiating accurately and efficiently the waveform changes attributed to alternation of motor units and activation of additional motor units through automation. When the ambiguity of alternation cannot be completely eliminated, it is incorporated into the final estimation of the MUN by reporting the statistical characteristics of the estimates.

In accordance with the present invention, methods and apparatus are provided for MUNE using an automated process. In one preferred form of the invention, the system comprises the following:

1. Application of Pre-configured Electrode Array. The electrodes necessary for delivering stimulation to the subject, and acquiring responses from the subject, are pre-arranged on a single housing so that a fixed geometric relationship between electrodes is controlled (i) during each study session and (ii) from study session to study session. The electrode array is applied according to anatomical landmarks of the subject.

2. Automated Data Acquisition. Stimulation and acquisition parameters are determined, adjusted, and controlled via an automation algorithm and the intermediate response characteristics.

3. Pre-processing Response Waveforms. The acquired response waveforms are batch-processed to remove artifacts, define motor unit activity range, calculate noise threshold, and consolidate identical motor unit responses. Noise threshold is used to identify waveforms that are different due exclusively to noise. The batch processing may be repeated with additional waveform acquisition.

4. Alternation Identification. One or more pre-processed response waveforms are examined at a time. Any changes between waveforms are identified as alternation of another motor unit or activation of a new motor unit. Two distinct approaches (Global Search and Direct Alternation Identification) are provided for identifying the changes, and can be used independently or in conjunction with one another. Both approaches are designed to differentiate the sources of waveform variations. Global Search determines the best possible explanation of a given experimental outcome in terms of motor unit activation and alternation. Direct Alternation Identification identifies alternating MU response waveforms and excludes incorrect subtraction between the alternating MU responses.

5. MUNE Calculation. MUN are estimated based on the size of SMUP and the size of maximum CMAP. An example of waveform size is its amplitude. When more than one MUNE result is possible, the distribution of the MUN estimates is described through its mean, standard deviation, and other statistical measures such as confidence interval.

The aforementioned steps are preferably performed using a commercially-available electrophysiological diagnostic device, and a general purpose computer provided with appropriate programming, or with a dedicated computer provided with appropriate programming, in a manner which will be apparent to those skilled in the art in view of the present disclosure.

The aforementioned steps of (1) Application of Pre-configured Electrode Array, (2) Automated Data Acquisition, (3) Pre-processing Response Waveforms, (4) Alternation Identification and (5) MUNE Calculation will hereinafter be discussed in greater detail.

1. Application of Pre-configured Electrode Array. The surface electrode array comprises a plurality of electrodes placed on the surface of the subject's skin according to known anatomical landmarks. For example, the distal wrist crest, shown at 53 in FIG. 4 is a known anatomical landmark example. The electrodes are pre-arranged on a single housing 50 (FIG. 4), insulated from each other, and held on the skin by an adhesive. The geometry between electrodes may be fixed or it may be variable in a controlled manner. The pre-configured electrode array has the advantage of acquiring a stable and more certain signal during each study session as well as from study to study. Electronic connection to an electrophysiological diagnostic device 52 is made through a keyed connector 51. A different housing, and different geometric specifications for the electrodes is provided for testing different muscle groups.

2. Automated Data Acquisition. Data acquisition setup includes stimulation parameters and recording conditions. An initial setup can be a default setting or adapted to specific demographics of a subject. Following each stimulus delivery, the response waveform acquired with detector electrodes 61, 62, and 63 (FIG. 4) is analyzed. Based on the history of all response waveforms, the data acquisition setup is modified automatically. The stimulation parameters include duration, intensity, polarity, frequency and other features of electric current. The recording conditions can be modified for waveform gain, starting and ending time of waveform recording, which recording electrodes are used, and other parameters. Adjustments are based on the feature space of the response waveforms including the absolute values of the features and changes in the absolute values from response to response. Modifications of the data acquisition setup are carried out in an automated manner with minimal or no operator intervention. As an example, if the most recently acquired waveform is identical to the waveform acquired previously, then the stimulus intensity is increased. If the changes between two acquired waveforms are larger than the changes previously obtained, the increase in stimulus intensity is reduced to ensure only one additional motor unit is activated. If the initial electronic connection is such that electrode 64 is the stimulator cathode and electrode 65 is the anode, the polarity of the stimulator is reversed by switching the electronic connections for 64 and 65 through a relay switch.

3. Pre-processing Response Waveforms. The acquired response waveforms may contain noise. The noise can be electronic or physiologic in nature. Some acquired waveforms may contain no motor responses related to a given stimulation. In addition, the useful time duration of the responses may be only a fraction of the duration of the total waveform. Pre-processing is thus conducted to remove the noise waveforms, attenuate the noise and identify the relevant activity regions so as to improve the computing speed and accuracy. A separately recorded maximum CMAP can be used to grossly define the region of activity for motor unit responses evoked by threshold stimulation. Waveform segments outside the activity region can be used to estimate noise level. A similarity measure is developed to determine whether variations between a pair of waveforms are substantial. Similarity measure can be a correlation coefficient between the two waveforms or a mean square difference between the two waveforms. Based on the similarity measure and the estimated noise level, response waveforms whose differences are attributable exclusively to noise are identified and consolidated for subsequent analysis.

4. Alternation Identification. Alternation poses a major challenge when using the IS method. The unidentified alternation waveforms can invalidate the motor unit count. The present invention presents two different methods for recognizing alternation patterns in a sequence of waveforms in response to the known and controlled stimuli.

(i) Global Search. Traditionally, a decision needs to be made, once a waveform is acquired, as to whether changes in the waveform are due to alternation or new motor unit activation. The Global Search method allows a decision to be deferred until multiple new waveforms are acquired. All feasible alternation and activation patterns are then constructed and ranked. The pattern or patterns with highest ranks are considered and SMUPs are extracted based on the recognized patterns. Representative SMUP waveform can then be constructed and relevant waveform features are computed. The steps include:

a. Decision Deferment. The deferment parameter specifies the number of waveforms that will be examined together in order to determine the best alternation and activation pattern. The parameter is set up in the search algorithm to balance the computing complexity and the pattern recognition performance. The parameter dictates how many additional waveforms need to be considered as a processing set used for determining alternations.

When the deferment level is set to one, the decision process becomes the step-by-step sequential manual processing. At the other extreme, if the level of deferment is set to be the same as the total number of waveforms acquired, the decision is made only after all possible combinations of alternation and activation are evaluated for all available waveforms. In effect, a higher deferment level allows for a global optimization solution instead of a sequence of local sub-optimal solutions.

b. Pattern Scoring. The alternation and activation pattern that best describes a sequence of recorded waveforms may not be obvious. Each possible pattern is contemplated by the Global Search method. A set of potential SMUP waveforms are derived from each alternation and activation pattern. A scoring system has been developed to rank the set of waveforms associated with each pattern. The quantitative ranking criteria (or scores) are designed to give a high numerical value for the waveforms matching desired features of the expected SMUP waveforms. As an example, the onsets of SMUP (feature 39 in FIG. 2) waveforms should be similar to each other and to the onset of the maximum CMAP (feature 49 in FIG. 2). A high numerical score is given to a set of waveforms if their onset values are similar to each other and to that of the maximum CMAP. In addition to the onset, other features may include amplitude (feature 38 in FIG. 2), duration, morphology, correlation with other SMUPs, etc.

c. Decision Process. SMUP waveform sets derived from all alternation and activation patterns are ranked via the aforementioned scoring systems. The decision process is provided to identify the SMUP waveform set associated with a pattern that has the highest score. The Global Search method allows several different patterns to co-exist as optimal solutions if they share the same high score. Each pattern has a distinct set of SMUP waveforms, from which pattern an estimate of MUN is made. Multiple sets of SMUP waveforms will provide a range of MUN estimates. The statistics (e.g., mean and standard deviation) of the estimates are calculated and then reported.

(ii) Direct Alternation Identification. The second approach for identifying alternation utilizes direct identification of the alternating MU response waveforms. If an alternation condition is satisfied by any response waveforms, these waveforms are identified as resulting from alternating MUs and should be excluded from SMUP calculations based on new motor unit activation. Therefore, the probability of misclassifying alternation events is reduced. The direct alternation identification procedure includes the following steps:

a. Alternation Equation Check. The MUs alternation waveforms are directly identified by checking the so-called "Alternation Equation". The Alternation Equation is an alternation condition that only alternating waveforms can satisfy. Therefore, the Alternation Equations are the indication that alternating of MUs has occurred. The identified alternating waveforms are excluded from the waveform pool to construct SMUP via direct subtraction. Instead, the alternating MU waveforms are used via Alternation Equations to extract potential SMUPs.

b. SMUPs Extraction and Validation. The aforementioned Alternation Equations detect alternating MU response waveforms. All of the alternating waveforms that have an overlap range form an alternation range. The recording of waveforms from a muscle group may involve many alternation ranges. As an example, as shown in FIG. 3, MU1 and MU2 form an alternation range, and MU3, MU4 and MU5 form another alternation range. In an alternation range, the potential Motor Units (or SMUPs) are extracted via Alternation Equations. Beyond the alternation ranges, the potential Motor Units are extracted using the traditional IS method.

The extracted potential SMUPs are validated by a self-check method. The method requires that, for each acquired response waveform, a subset of the extracted SMUPs must exist so that their summation will match the response waveform. Otherwise, the mis-matched recording waveforms are as considered containing new SMUPs, and thus required for further examination. The final SMUP selection is a subset of SMUPs that has a minimum number of SMUPs, but matches all the acquired response waveforms.

5. Motor Unit Number Estimation. Motor unit number estimation is based on features from maximum CMAP and the SMUP waveform set identified via either the Global Search approach or the Direct Identification approach. The feature (such as waveform amplitude) is calculated for each SMUP waveform and the set of features are combined (e.g., averaged) to obtain an estimate of the feature useful for MUNE. Alternatively, the set of SMUP waveforms can be consolidated with means like weighted averaging, followed by computation of the relevant features for the consolidated waveform. A third approach calculates the feature of the original response waveform with the highest number of known SMUP components. The feature is then weighted by the SMUP component count. The same feature is calculated for the maximum CMAP waveform. The estimate of motor unit number is then the ratio between the features of the maximum CMAP and SMUP waveforms. It is possible that Global Search method will yield more than one set of SMUP waveforms. If this is the case, multiple estimates of MUN will be obtained. Statistical description of these estimates, such as mean and standard deviation, are then calculated to describe the MUN estimates.

In another form of the present invention, there is provided a method for the assessment of neuromuscular function by the estimation of motor unit numbers, comprising:

interfacing an electrode array with the subject for the purpose of delivering one or more controlled stimuli using at least one stimulator electrode and acquiring electric activity signals of one or more motor units using at least one detector electrode;

delivering a stimulus of varying characteristics to the subject;

identifying and eliminating any acquired signals due to alternation; and automatically estimating motor unit number based on the consolidated acquired signals using an automation algorithm.

In additional form of the present invention, there is provided apparatus for the assessment of neuromuscular function by the estimation of motor unit numbers, comprising:

stimulator apparatus for delivering electrical stimuli to a subject;

detector apparatus for acquiring the electrical signals from one or more motor units;

alternation elimination apparatus for automatically eliminating acquired electrical signals due to alternation; and automatic estimation apparatus for automatically estimating motor unit number based on the remaining acquired signals.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 5:
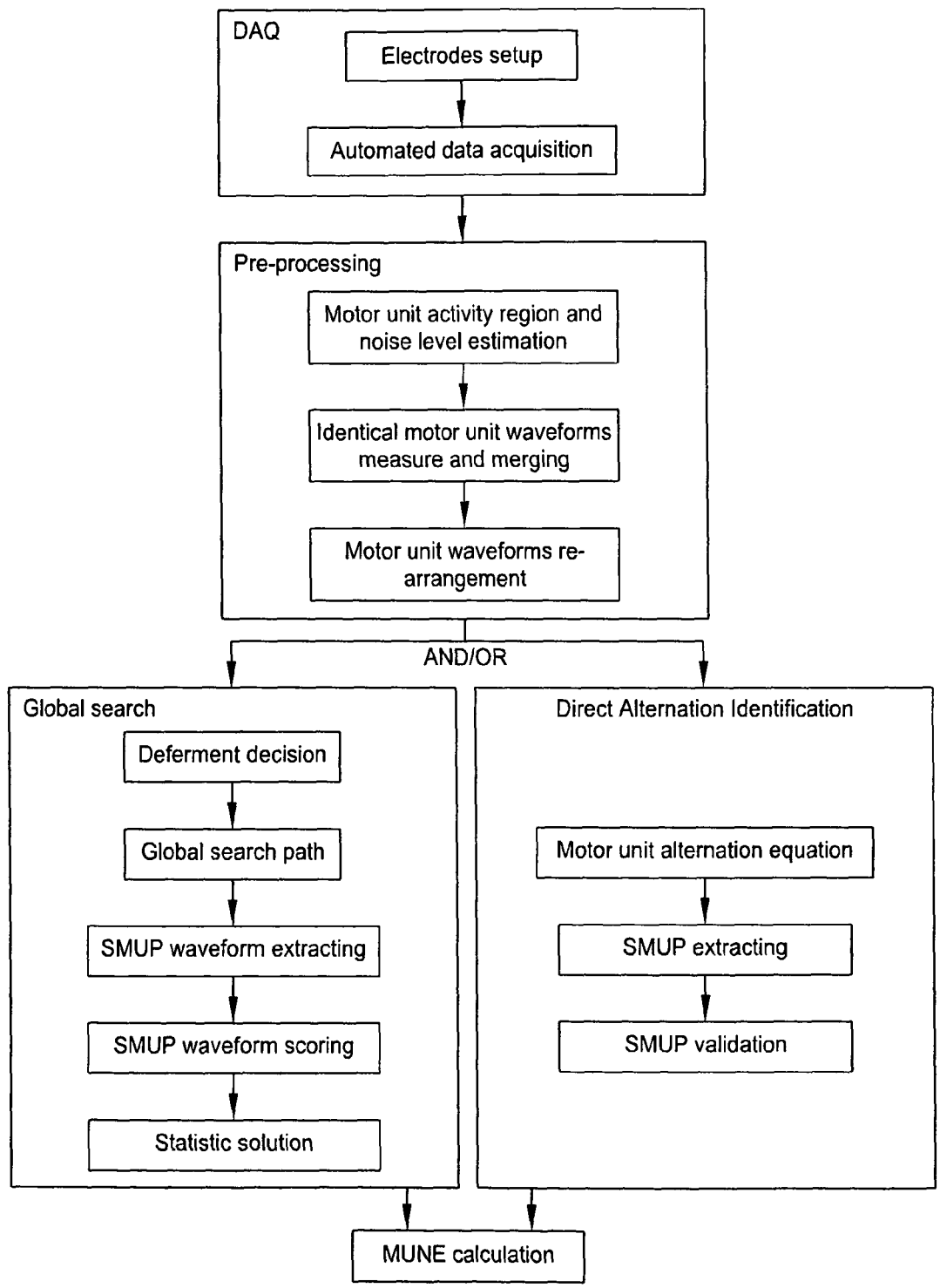
FIG. 5 illustrates, in the form of a top-level flow chart, the preferred methodologies of the present invention.

MUNE is a technology developed to evaluate neuromuscular functions. As noted above, MUNE automation using the traditional IS method needs to address the issue of motor unit alternation. The present invention provides an automation method to estimate MUN more accurately and reliably by minimizing the adverse effect of alternation based on waveforms acquired with pre-configured electrode array under controlled stimulation conditions. The methodology of the preferred embodiment of the invention is illustrated in FIG. 5.

Figure 4:
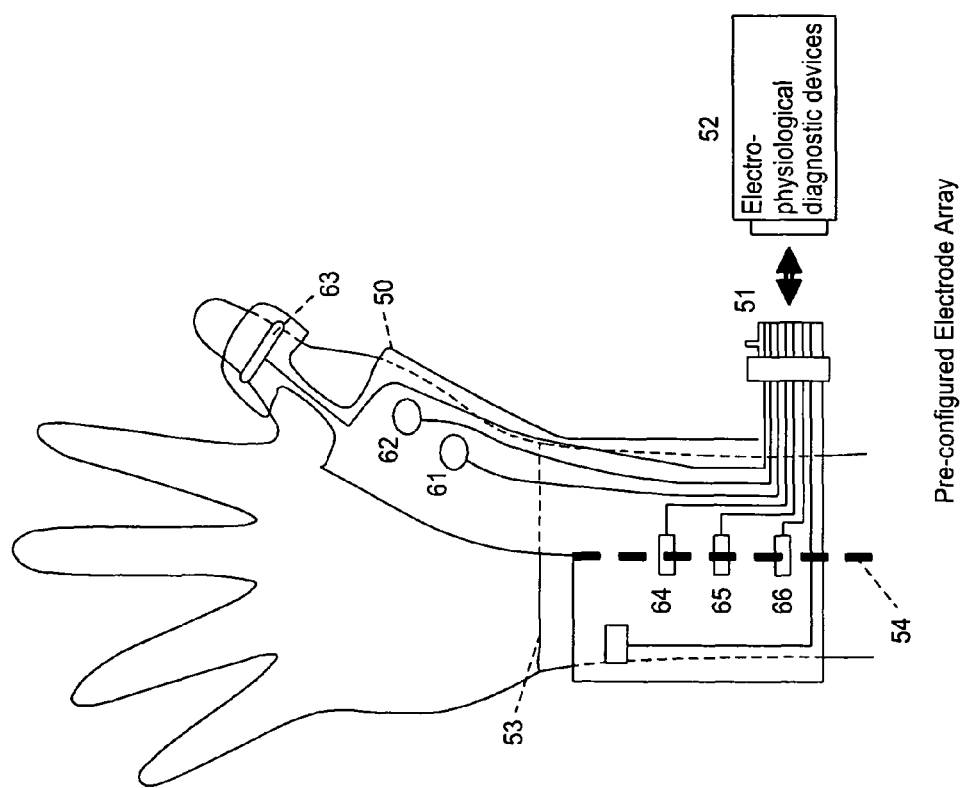
FIG. 4 illustrates the structure of a pre-configured electrode array used in accordance with the present invention.

1. Pre-configured Electrode Array. A surface electrode array 50 (FIG. 4) consists of pre-arranged electrodes on a single housing. The array is placed on the surface of skin of the subject according to anatomical landmarks (e.g., distal wrist crest 53 in FIG. 4). The electrodes are used to deliver stimuli and to acquire response waveforms. The stimulator portion of the electrode comprises two or more electrodes 64, 65, and 66 (FIG. 4). The stimulator electrodes are placed over or near the nerve axons which are to be stimulated (e.g., median nerve 54 in FIG. 4). The geometric relationship between stimulator electrodes are controlled, fixed and known. Through electric circuit design, each electrode is connected as a cathode and one of the remaining electrodes is connected as an anode. Alternatively, more than one electrode can be connected as cathode or anode. The ability to alter anode and cathode electrode connections allows a greater diversity in electric current patterns delivered to nerve axons. This diversity, combined with fine control of varying electric current intensity, provides a greater assortment of stimulated axons. As a result, a better sampling of motor units is achieved.

Multiple electrodes are used to acquire response waveform (e.g., electrodes 61, 62, and 63 in FIG. 4). The spatial associations of the signal acquisition electrodes with respect to each other are fixed and known (or is controlled with accuracy). The spatial relationship of the signal acquisition electrodes with respect to stimulator electrodes is also fixed. After the application of each stimulus, more than one response waveform can be acquired through a different pairing of detection electrodes. As an example, two response waveforms may be acquired simultaneously, one from electrode pair 61 and 63 and the other from electrode pair 62 and 63.

All electrodes are insulated from each other and held on the skin with an adhesive. From the electrode array, with known and fixed geometric associations among all electrodes, stable and more certain response waveforms are acquired during each study session as well as from study to study.

2. Automated Data Acquisition. An electrodiagnostic device acquires motor responses via detection electrodes of the electrode array. The motor responses are evoked by the activation of the nerve axon under the stimulus electrode when a controlled electric shock is delivered to the nerve via stimulus electrodes.

The motor responses (both SMUP and CMAP) are acquired with adjustable analog gain so that the response range spans the dynamic range of the data acquisition system. The responses are also optionally filtered to reduce the measurement noise outside the primary energy band of the motor responses. A significant portion of motor response energy lies in the frequency range of 30-800 Hz. To avoid aliasing, the analog response waveform is lowpass filtered and sampled at rates in excess of twice of its Nyquist frequency. As an example, if the CMAP is filtered with a lowpass filter of 2500 Hz, the waveform is sampled at a rate at or greater than 5000 Hz.

Figure 6:
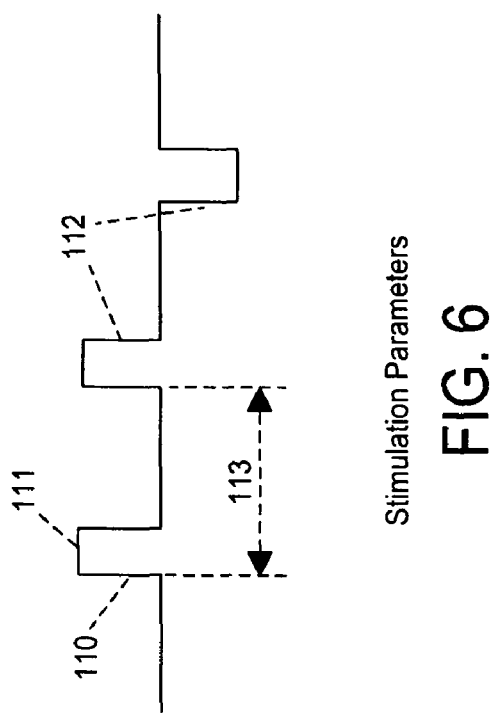
FIG. 6 illustrates the setup of stimulation parameters for MU stimulus.
Figure 7:
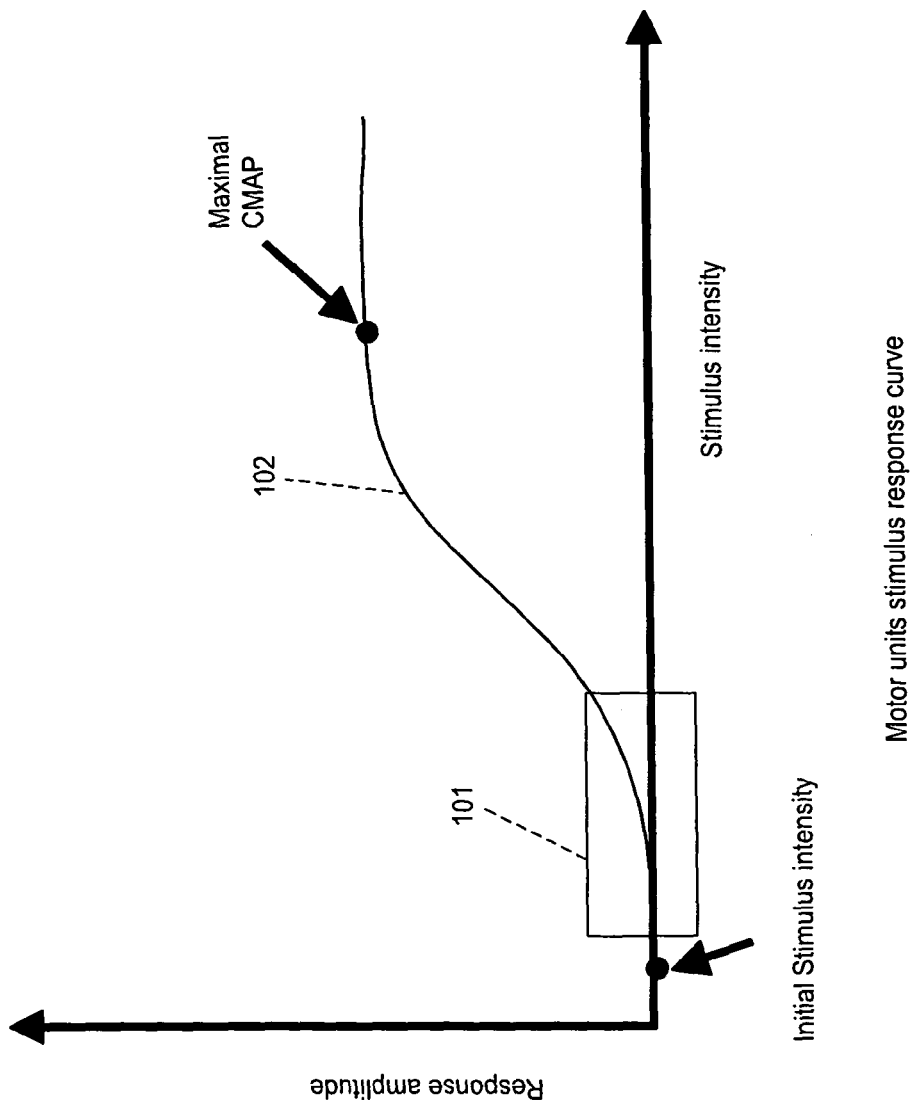
FIG. 7 illustrates motor units stimulus responses.

The stimulation parameters may depend upon the subject demographics. For example, higher stimulus intensity is used when the subject has an above-average body mass index. The body mass index correlates with adipose tissue volume. A higher body mass index is a good predictor of a thicker layer of adipose tissue separating skin and nerve axon, and therefore a higher stimulus intensity is needed to activate the axon. The stimulation parameters depend upon the prior electrophysiological responses. For example, a stimulus response curve 102 (FIG. 7) for the nerve under study is generally available when stimuli with a gradual increase in intensity are delivered to obtain maximum CMAP response. The IS method operates at the threshold region 101 (the boxed area of the stimulus response curve shown in FIG. 7). Using the electrode placement arrangement identical to that for acquiring maximum CMAP response, the IS response waveforms are acquired. The stimulation parameters are digitally controlled with finer precision (e.g., 0.1 mA increments in stimulus intensity). More than one stimuli of the same intensity are delivered to the nerve axon in order to elicit responses from distinct motor units with overlapping activation thresholds. The control of the stimulation parameters is tightly integrated with the subsequent waveform analysis procedures. If alternation activities are detected and cannot be separated effectively from activation activities, an even finer stimulus intensity increment is used to differentiate the motor units with overlapping activation threshold. In addition to stimulus intensity 110 (FIG. 6), other controllable and adjustable parameters include duration 111, polarity 112, and repetition interval 113. For example, instead of stimulus intensity adjustment, both duration and intensity are altered simultaneously to attempt to evoke different motor units. The real-time integration of response waveform analysis and data acquisition control improves the efficiency, accuracy, and reliability of the MUNE.

Figure 1:
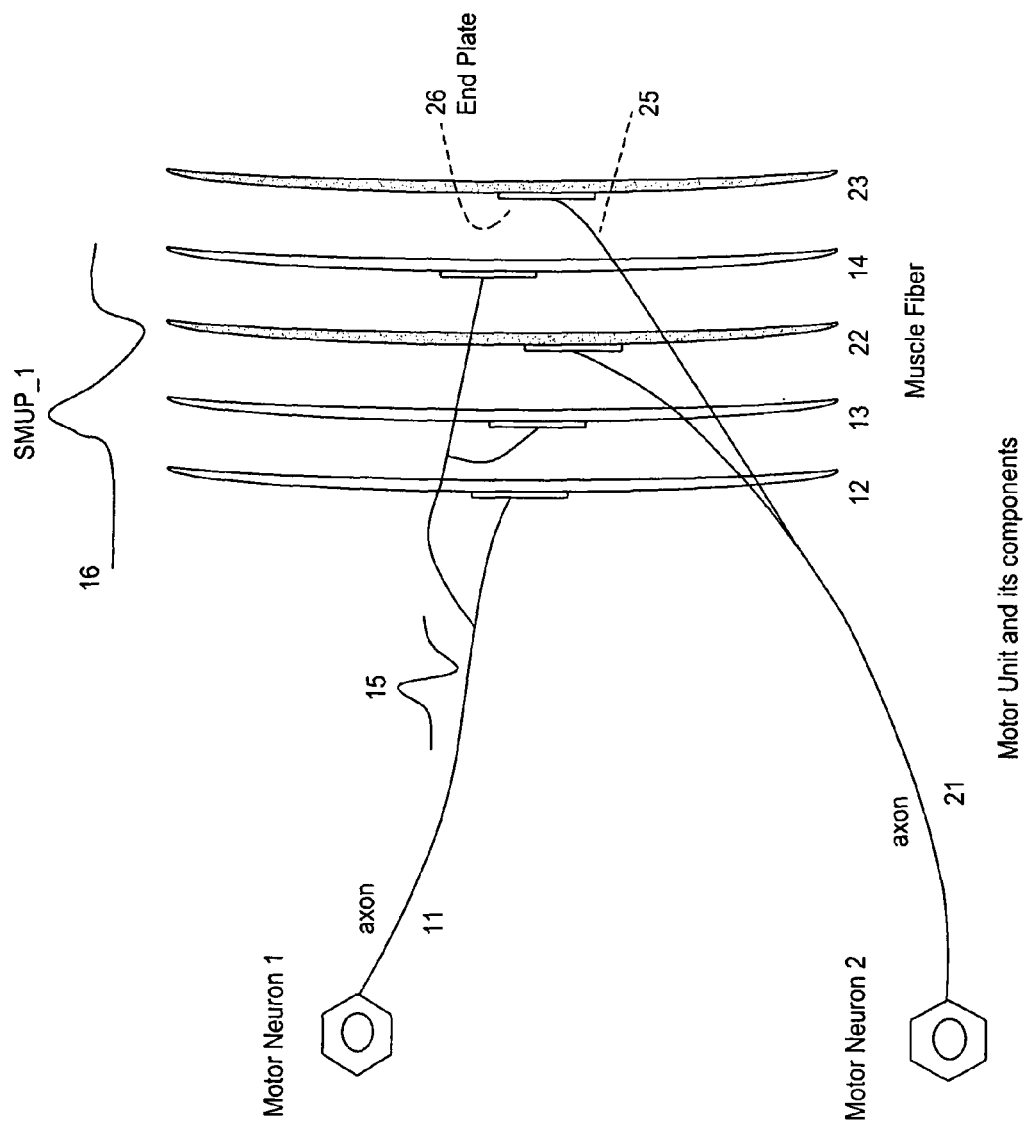
FIG. 1 illustrates Motor Unit structure and its components.
Figure 2:
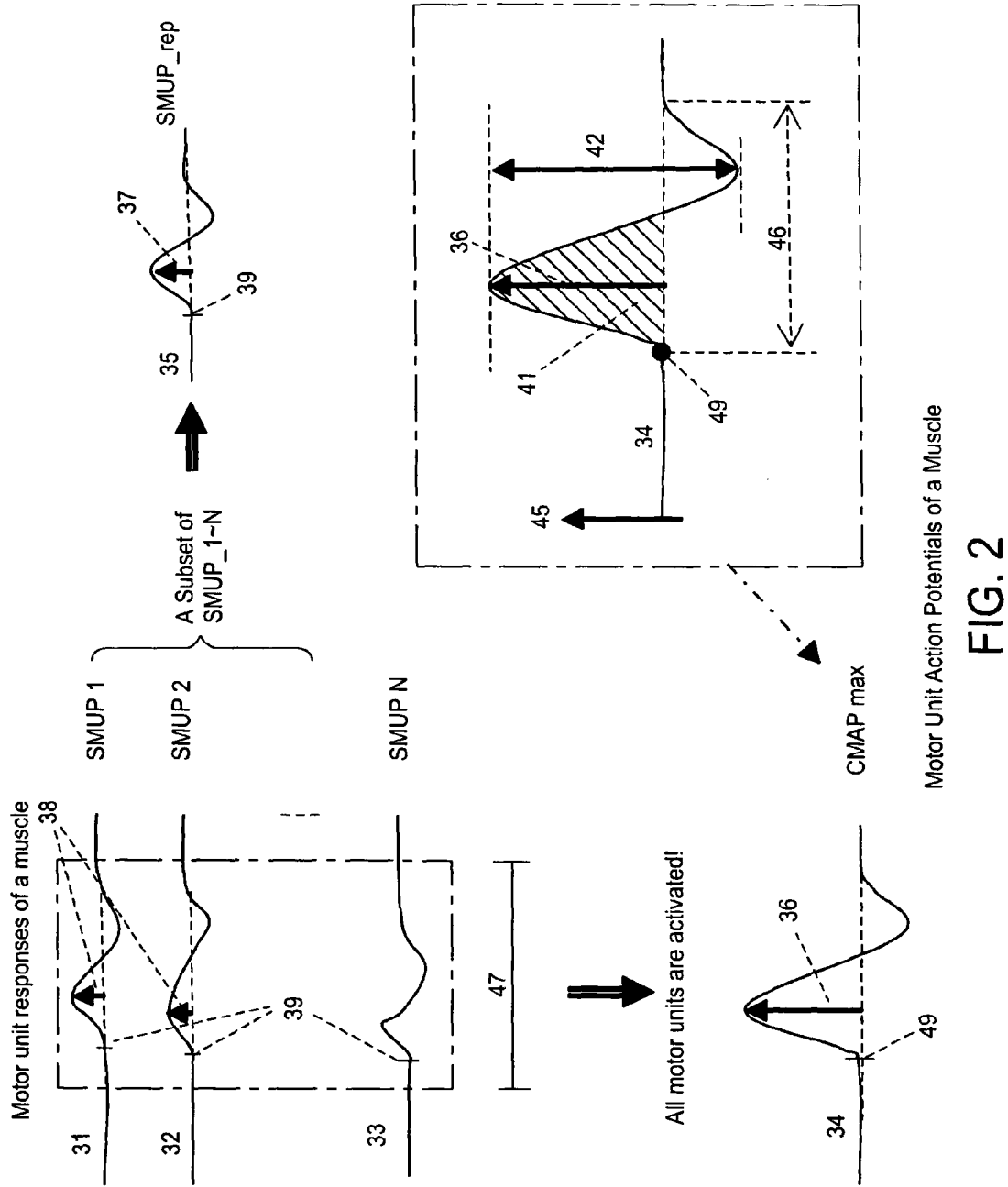
FIG. 2 illustrates Single Motor Unit Potentials (SMUPs), average of SMUPs, and Compound Motor Unit Potential (CMUP)
Figure 3:
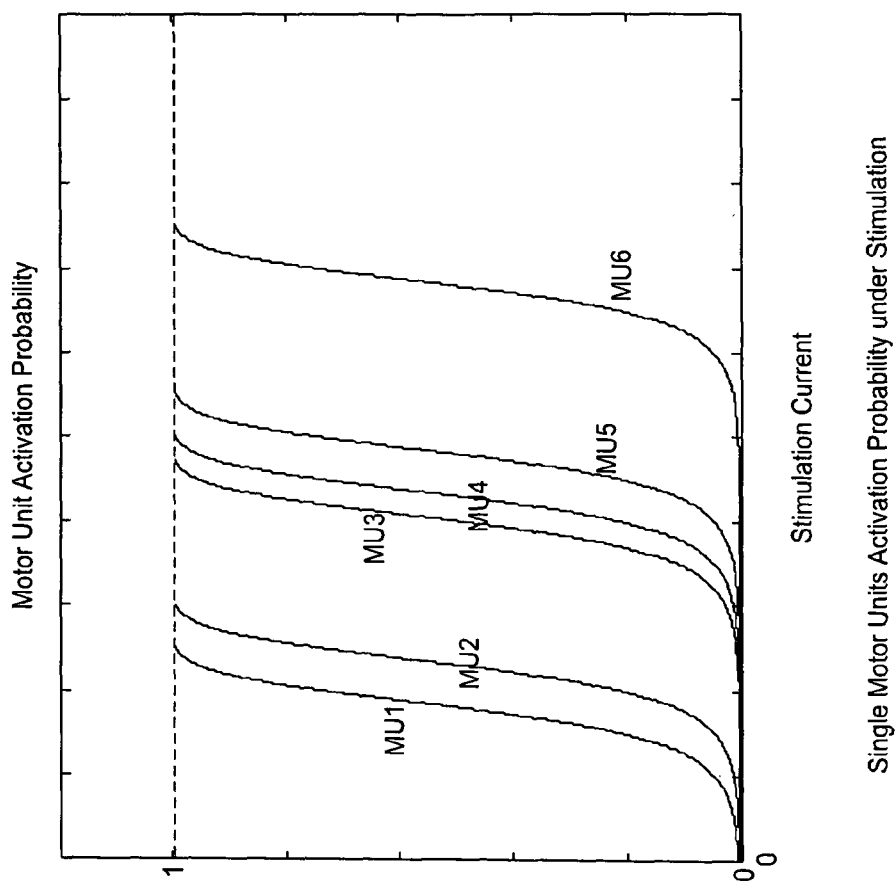
FIG. 3 illustrates Motor Units Alternation phenomena.

3. Pre-Processing.
   i. MUs Activity Region Determination and Noise Estimation. The baseline and any DC offset of the acquired response waveforms are removed. The onset 49 (FIG. 2) and the duration 46 (FIG. 2) of the maximum CMAP are used to determine the response activity region 47 (FIG. 2). The response activity region 47 is searched within the maximum CMAP duration. In this search, the absolute deviations of the response waveforms from their median are averaged across waveforms at each time sample so as to form an activity profile. The region of the activity profile where the value exceeds the noise level defines the response activity region. Segments of the response waveform falling outside the activity region are no longer considered in the MUNE analysis. The waveform segment outside of the maximum CMAP region is used to estimate background noise. The noise power is calculated and a multiple of the noise power is then used to screen response waveforms. Any waveform having a power less than this threshold is considered a null response waveform and is removed from further analysis.

ii. Identical Waveform Measure And Merging. A similarity measure is used to evaluate whether the differences between two waveforms are exclusively due to noise. The measure is based on Euclidian distance and is calculated as follows: the sample-by-sample difference between the two waveforms are calculated and squared; the squared difference values are added; and the summation is divided by the number of samples or the length of the waveform. Measures based on other metrics such as mean absolute value and correlation coefficient are also possible.

The similarity of a given pair of waveforms is compared with the noise threshold. A pair of waveforms is considered as having identical responses if the similarity measure is below the noise threshold. The identical waveforms are then combined to produce a single, consolidated waveform for subsequent analysis. Waveform combination is done by averaging the two waveforms. Consolidated waveforms have better waveform quality and reduced noise. Waveform combination also improves the efficiency of alternation pattern determination process by reducing the number of waveforms to be examined.

iii. Waveforms Sorting. The response waveforms are sorted by waveform energy and the stimulus intensity to facilitate alternation identification.

4. Global Search.
   i. Deferment Decision Level. Because of the possibility of alternation, morphological differences between consolidated response waveforms cannot be automatically attributed to activation of additional motor units. A decision has to be made as to whether waveform variations are due to the activation of a new motor unit or due to alternation. Previously, such a decision would generally be made sequentially, based on manual examination of each pair of waveforms.

In the Global Search method, the decision is deferred in order to assess consequence of either possibility (new motor unit or alternation) by considering more than two waveforms.

The level of decision deferment (i.e., how many additional waveforms need to be considered before a decision is made) is controlled via automation parameter settings. When the level of deferment is set at one, then the decision process utilizes step-by-step sequential manual processing. Global Search with a deferment level of two will determine the best path of alternation or activation based on two new response waveforms. When the level of deferment is set to be the same as the total number of acquired waveforms, the decision is made only after all possible combinations of alternation and new motor units are considered. A higher deferment level will lead to a better discrimination of alternation activities, and thus a more accurate estimate of motor unit number. However, a greater computational complexity is associated with a higher deferment level.

ii. Global Search Paths. The Global Search method evaluates all possible combinations of SMUPs at a pre-set decision deferment level. The approach is illustrated with an example below (shown in FIG. 8). If the deferment level is one, a decision is made as to whether the changes in $x_2$ is a result of new motor unit or alternation.

Figure 8:
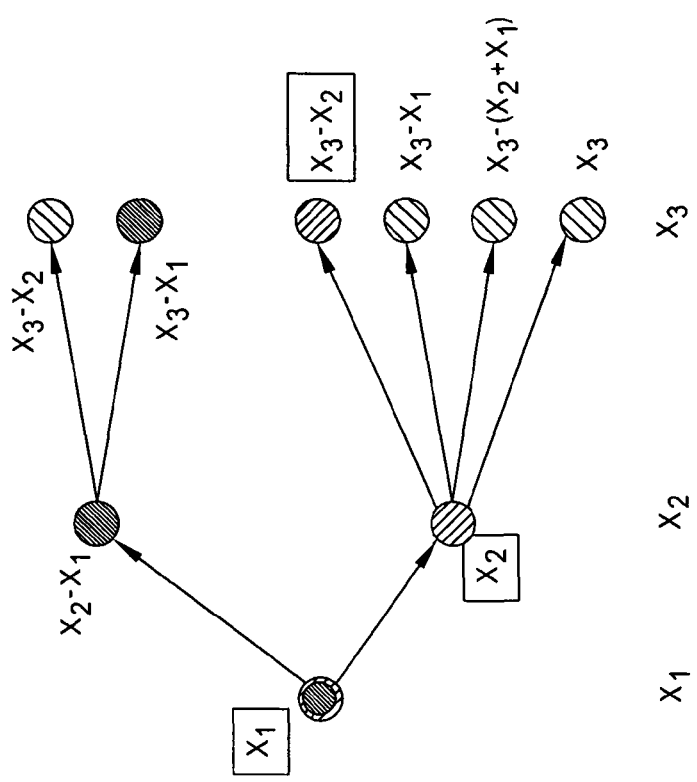
FIG. 8 illustrates the deferment of the decision process involved in the global search strategies.

The scores of the two candidate paths are calculated (see waveform scoring section): $\{x_1, x_2-x_1\}$ and $\{x_1, x_2\}$. The path with a higher score is selected. If the path $\{x_1, x_2-x_1\}$ is selected, the next step is to form candidate paths that include $x_3$: $\{x_2-x_1, x_3-x_1\}$ ($x_3$ is a result of alternation) and $\{x_2-x_1, x_3-x_2\}$ ($x_3$ is a result of new activation). The scores for the two paths are calculated and the path with a higher score is selected. If more response waveforms are available, the process is repeated for all other waveforms. The lower half of the candidate paths shown in FIG. 8 are not considered further by the search algorithm once the boxed $x_2$ node is excluded from the first segment of path.

If the deferment level is greater than one (e.g., two), no commitment needs to be made at the $x_2$ level until $x_3$ is observed. This will allow the evaluation of all paths shown in FIG. 8. When candidate paths are constructed, the path $\{x_1, x_2, x_3-x_2\}$ will be one of them. A score may be higher than $\{x_1, x_2-x_1, x_3-x_1\}$, suggesting that the path with boxed nodes is a better solution. In effect, a higher deferment level allows for a global optimization solution instead of a sequence of local optimization solutions.

iii. SMUP Waveform Extracting. For each search path, a set of SMUPs are obtained, depending upon the assumption made to form that path. For example, if it was assumed that the path consists of all new motor unit activities from one node to another, the SMUPs will be differences between successive response waveforms associated with each node (for the most top path in FIG. 8).

iv. SMUP Waveform Scoring. Multiple candidate paths are formed as a result of decision deferment. The candidate SMUP waveform set obtained from each path is scored based on ranking criteria. All candidate paths are ranked based on the scores of the candidate SMUP waveforms associated with the paths. The quantitative ranking criteria capture the desired features of true SMUPs. A set of SMUPs receive a higher score if the individual SMUP waveforms meet the criteria of initial negativity (up peak followed by down peak) and biphasic morphology. A similar onset for all SMUP waveforms will yield a higher score as well. In the case that two successive response waveforms are due to alternation but the path search dictates that they are considered as new motor unit activation, the candidate SMUP derived from the path will be the difference between the two individual motor unit responses. Thus, it will likely have smaller amplitude, irregular morphology, and perhaps a delayed onset time because of the phase cancellation. Consequently, the score for the candidate SMUP will be low and the incorrect candidate path will be penalized with a lower score. Additional scoring components for candidate SMUP waveforms include: the offset of a SMUP waveform power over the average power level of all SMUPs;

the offset of a SMUP waveform onset over that of the CMAP;

the offset of a SMUP waveform duration over that of the CMAP;

the offset of a SMUP waveform maximum negative peak location over that of the CMAP;

the offset of the waveform numbers of this SMUP group over the total number of consolidated MU waveforms.

Each feature is weighted by a weighting factor that is consistent in determining its relative importance to other features. The weighting factors are based on prior data analysis, physiological factors, and other considerations. The weighted feature scores are summed for all features and all SMUPs to form the final ranking score for a group of SMUPs.

Figure 9:
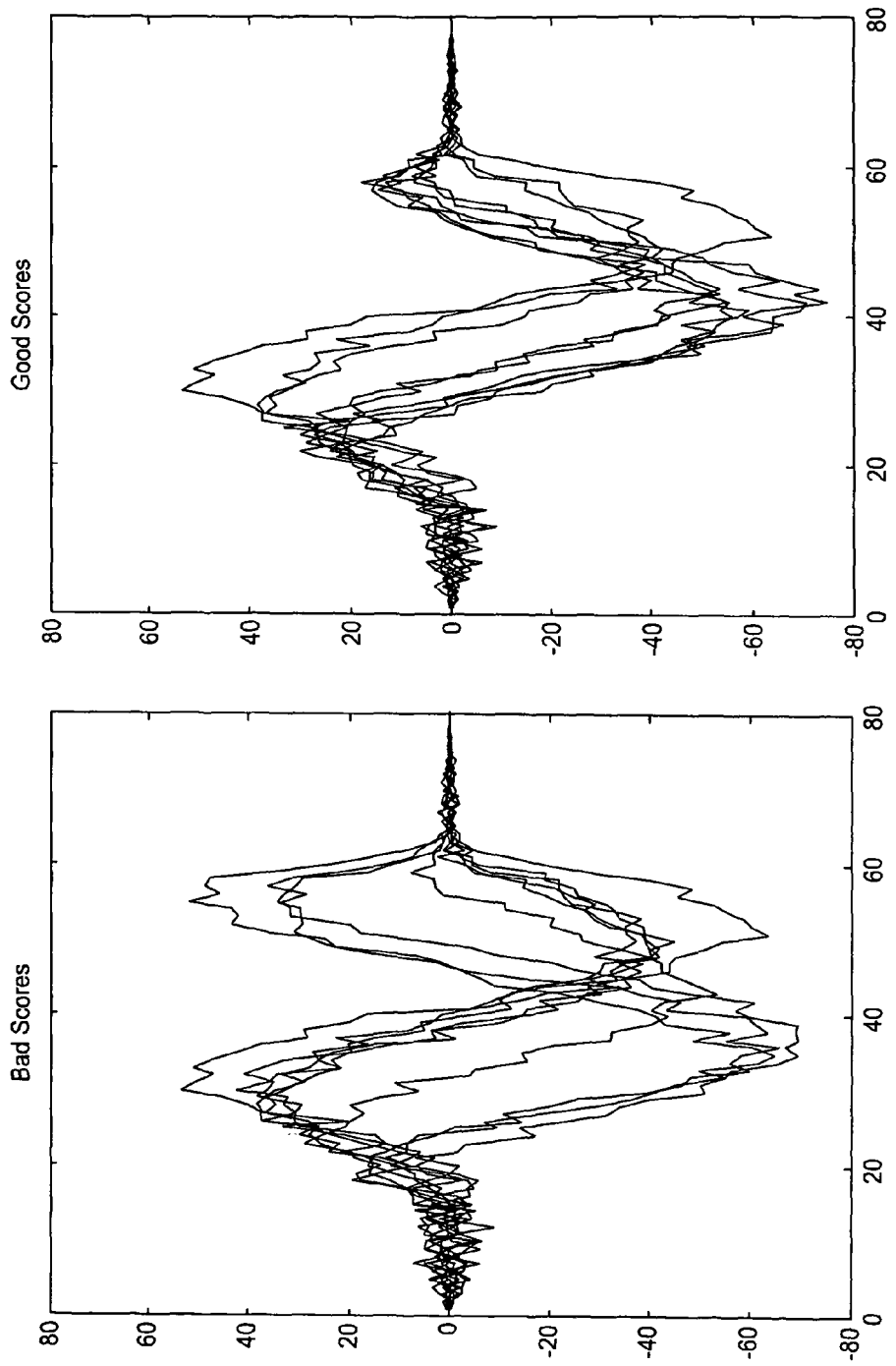
FIG. 9 illustrates the motor unit potentials scoring example involved in the global search strategies.

FIG. 9 shows two groups of SMUPs: the left panel shows a group of SMUPs with a lower ranking score, and the right panel shows a group of SMUPs with a higher ranking score.

5. Direct Alternation Identification (i) MUs Alternation Equation. As an example, a frequently observed alternation pattern is shown in Table 1 where two motor units (MU3 and MU4) alternate before both of them are activated together. The first column is the recording waveforms, and the second column describes the individual MUs included in these recordings. Direct subtraction of the MUs responses would result in creating three motor units: $MU_3=x_1-x_0$, $MU_4{}^a=x_2-x_1=MU_4-MU_3$, and $MU_5=x_3-x_2=MU_3$. As a result, $MU_4{}^a$ will be an under-estimation of $MU_4$, leading to an over-estimation of MUNE. To identify the alternation patterns, one first removes the common component $x_0$ ($MU_1+MU_2$) to obtain residuals $r_i=x_i-x_0$, i=1,2,3. The residuals $r_i$, i=1,2,3 and their MUs are listed in the third and fourth columns of Table 1, respectively. These residuals satisfy the following Alternation Equation:

$$r_1+r_2=r_3.$$

The above equation condition indicates that alternations are present in the recording waveforms $x_1$ and $x_2$. Subsequently, $x_2-x_1$ is not a true SMUP. Instead, the components $r_1$ and $r_2$ are considered as potential motor units for further evaluation.

TABLE 1

Illustration Of The Alternation Equation Check Method

| MU response recordings | Motor Unit components | Residual waveform | Motor Unit components |
|---|---|---|---|
| $x_3$ | MU1 + MU2 + MU3 + MU4 | $r_3$ | MU3 + MU4 |
| $x_2$ | MU1 + MU2 + MU4 | $r_2$ | MU4 |
| $x_1$ | MU1 + MU2 + MU3 | $r_1$ | MU3 |
| $x_0$ | MU1 + MU2 | | Base waveform |

In general, for a set of consolidated recording waveforms $x_0, x_1, \ldots x_l$, $\forall l \geq 3$, one needs to remove the common component $x_0$ to obtain residual signals $r_i=x_i-x_0\neq\phi$, i=1, ..., l, $\forall l \geq 3$. If the residual components $r_i$ satisfy the Alternation Equation:

$$\sum_{i\in J, j\neq i, j\in[1,\ldots,l]} r_i = r_j, \quad (1)$$

(here index set J is a subset of [1,2, ..., l]), then these components $r_i$, i∈J, are candidates to be assessed as alternating motor units. Direct subtraction between their original waveforms $x_i$, i∈J should be avoided.

Figure 10:
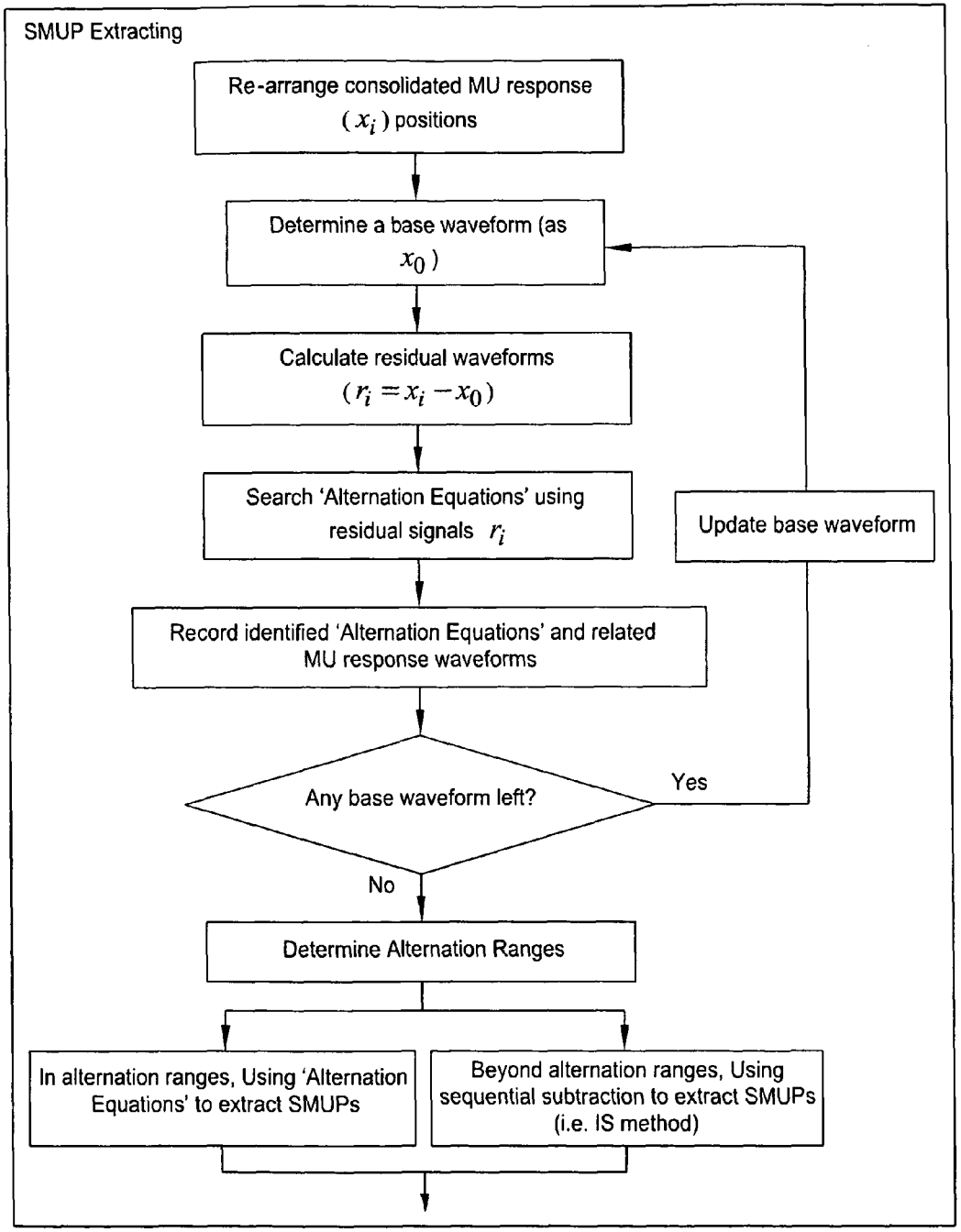
FIG. 10 illustrates, in the form of a flow chart, the SMUP extracting process using the Alternation Equation identification method.

(ii) SMUPs Extracting And Validation.

a. Potential SMUPs Extracting. The flow chart in FIG. 10 describes the methods of extracting potential SMUPs by using Alternation Equations.

In this step, all the consolidated MU response waveforms $x_i$, are re-arranged at different positions according to their power. The large power waveforms are placed on high positions. The base waveform (aforementioned common components among the MU responses) is first considered as a null signal, and then each of the MU response waveforms $x_i$ is tested once as a base waveform. At each determined base waveform position, the residual components $r_i$, are obtained by subtracting the base waveform from all those MU response waveforms which are at a higher position than that of this base waveform. This set of residual waveforms is checked using Alternation Equations (1). The residual waveforms that satisfy an "alternation equation" are identified and recorded. This procedure is repeated until all the MU response waveforms have been used as the base waveforms.

Those residual components of $r_i$ satisfying Alternation Equations indicate a fact that their corresponding original MU waveforms $x_i$ are alternating MU response waveforms. All of the alternating waveforms that have an overlap range form an alternation range. The recording waveforms from a muscle group may contain many alternation ranges. In any particular alternation range, the smaller residual waveforms on the left side of the Alternation Equations (1) are taken as potential SMUPs. Beyond the alternation ranges, the potential SMUPs are extracted using traditional IS method, i.e., a potential SMUP is extracted by directly subtracting an MU waveform from another MU waveform that is one position above.

The procedure discussed above can be further explained using the following example. Table 2 shows a case involving 5 alternating Motor Units: MU1-MU5. The first column lists the recording MU response waveforms $x_i$. The first (i.e., lowest) waveform $x_0$ has the least power, and the last (i.e., highest) waveform $x_9$ has the largest power. The second column describes their corresponding motor unit components. While waveform $x_0$ is determined as the base waveform, the residual waveforms are obtained by subtracting the base waveform $x_0$ from all the higher position waveforms from $x_1$ to $x_9$. The resulting residual waveforms $r_i$, i=1, . . . , 9, and their corresponding components, are listed in the third column and fourth column, respectively.

Then, these residual signals $r_i$, i=1, . . . , 9 are tested using "alternation equations (1)". Five alternation equations are found, and they are:

$r_1+r_2=r_5;$ $r_1+r_2+r_3=r_6;$ $r_1+r_2+r_4=r_8;$ $r_3+r_5=x_6;$ $r_4+r_5=r_8$

Those residual waveforms only presenting on the left side of the above equations are extracted as potential SMUPs. Accordingly, they are: $r_1$ (MU1), $r_2$ (MU2), $r_3$ (MU3), and $r_4$ (MU4). The residual waveform $r_5$ (MU1+MU2) appears on both sides of the equations, thus it cannot be a SMUP. These five alternation equations relate to seven response waveforms from $x_1$ to $x_6$, and $x_8$. These seven MU response waveforms form an alternation range including waveforms from $x_1$ to $x_8$. Beyond this range, only one recording waveform exists, which is $x_9$.

Figure 11:
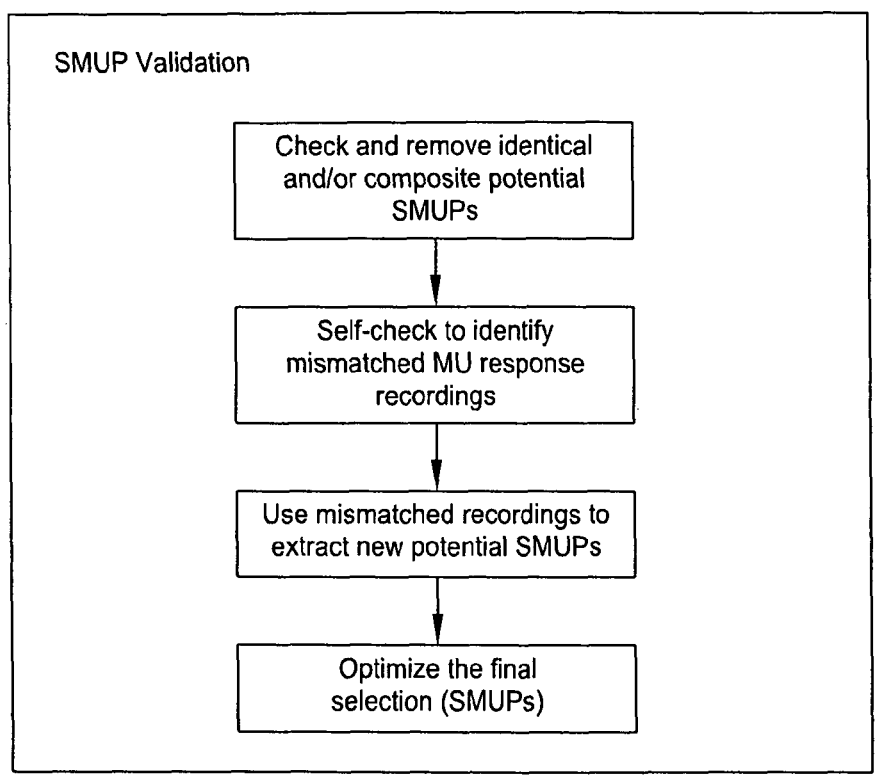
FIG. 11 illustrates, in the form of a flow chart, the SMUP validating process using the self-check method.

Within this alternation range, the direct subtraction among the alternating waveforms from $x_1$ to $x_8$ is avoided. Beyond this alternation range, traditional IS method is used. That is, the waveforms sequential subtraction result is taken as potential SMUPs, which result in $x_9-x_8$ (MU3+MU5-MU2).

b. SMUPs Validation. The flow chart in FIG. 11 describes the methods of SMUP validation by using self-check method. This process is explained as follows.

The aforementioned SMUP search process has extracted a group of potential SMUPs, and they are $r_1$ (MU1), $r_2$ (MU2), $r_3$ (MU3), $r_4$ (MU4), and $x_9-x_8$ (MU3+MU5-MU2). These potential SMUPs do not include all the true motor units (MU5 is missed), and also contain potential SMUPs that are not true motor units ($x_9-x_8$ is not a correct one).

To validate the potential SMUPS, firstly, identical waveforms or any composite SMUP waveforms (combinations of other SMUPs) are identified and removed from this potential SMUP group. In the above example, none of candidate waveforms are removed. The potential SMUPs are $r_1$ (MU1), $r_2$ (MU2), $r_3$ (MU3), $r_4$ (MU4), and $x_9-x_8$ (MU3+MU5-MU2).

TABLE 2

Illustration Of The SMUPs Extraction And Validation

| MU response recordings | Motor Unit components | Residual waveform | Motor Unit components |
|---|---|---|---|
| $x_9$ | $x_0$ + MU1 + MU3 + MU5 + MU4 | $r_9$ | MU1 + MU3 + MU5 + MU4 |
| $x_8$ | $x_0$ + MU1 + MU2 + MU4 | $r_8$ | MU1 + MU2 + MU4 |
| $x_7$ | $x_0$ + MU1 + MU2 + MU5 | $r_7$ | MU1 + MU2 + MU5 |
| $x_6$ | $x_0$ + MU1 + MU2 + MU3 | $r_6$ | MU1 + MU2 + MU3 |
| $x_5$ | $x_0$ + MU1 + MU2 | $r_5$ | MU1 + MU2 |
| $x_4$ | $x_0$ + MU4 | $r_4$ | MU4 |
| $x_3$ | $x_0$ + MU3 | $r_3$ | MU3 |
| $x_2$ | $x_0$ + MU2 | $r_2$ | MU2 |
| $x_1$ | $x_0$ + MU1 | $r_1$ | MU1 |
| $x_0$ | Base waveform (common components) | | |

Illustration Of The SMUPs Extraction And Validation

Secondly, a self-check method is provided. That is, if the potential SMUP combinations with the original base waveform $x_0$ are used to compare with the recording waveforms $x_1$, at least one subset of potential SMUPs must exist and their summation matches a given recording waveform. Otherwise, the recording waveform without a match must have a new SMUP component. In Table 2, a self-check can identify waveform $x_7$ does not meet the matching criteria. Thus, it must contain new potential SMUPs.

Then, the mis-matched waveforms are used to obtain additional SMUPs. The mismatched waveform subtracts lower level waveforms sequentially to obtain new residual waveforms. If a newly obtained residual waveform can be combined with existing SMUP candidates to match two or more recording waveforms, the new residual waveform is added to the potential SMUP pool.

As noted above, waveform $x_7$ is a mis-matched waveform. New residual waveforms are formed by subtracting lower position waveforms from waveform $x_7$. Two residual waveforms $x_7-x_5$ (MU5) and $x_7-x_2$ (MU1+MU5) meet the matching criteria twice for waveform $x_7$ and $x_9$. Thus, they are added to the potential SMUP pool. Now, the potential SMUPs group consists of $r_1$ (MU1), $r_2$ (MU2), $r_3$ (MU3), $r_4$ (MU4), $x_9-x_8$ (MU3+MU5−MU2), and new potential SMUPs $x_7-x_5$ (MU5) and $x_7-x_2$ (MU1+MU5).

After this self-check process, identical waveforms and composite SMUP waveforms are detected and removed. In this example, $x_7-x_2$ (MU1+MU5) is the combination of $r_i$ (MU1) and $x_7-x_5$ (MU5), and thus removed. The final selection is a set of SMUPs from the potential SMUP group that has a minimum number of SMUPs, but matches all the consolidated MUs responses. This last step can exclude incorrect waveforms $x_9-x_8$(MU3+MU5−MU2), and keep the true motor units which are $r_1$ (MU1), $r_2$ (MU2), $r_3$ (MU3), $r_4$ (MU4), and $x_7-x_5$ (MU5)

6. Motor Unit Number Estimation. MUNE is used to estimate the number of SMUP waveforms that will take to match the maximum CMAP waveform. Each SMUP is from an individual motor unit and the maximum CMAP is the result of all motor units in the muscle group. A specific feature of the waveform is used for matching waveforms instead of the total waveform morphology. For example, if the peak-to-base amplitude of a SMUP is 20 uV and the amplitude for CMAP is 5 mV, then the number of SMUP waveforms needed to match the CMAP is 250. Commonly-used measures for waveform size are peak-to-base amplitude, peak-to-peak amplitude, and peak area of SMUP and CMAP waveforms. The SMUP waveforms extracted from response waveforms do not have the same morphology and the size feature from each SMUP waveform is also different. Different methods are used to obtain the average SMUP feature:

Calculating the features of each SMUP waveform, and then average individual features;

Averaging all the SMUP waveforms, and then calculating the feature of the averaged SMUP;

Calculating the size feature of the largest response waveform with a known number of motor units, and then normalizing the value of the feature by the number of motor units.

Global Search method provides multiple sets of SMUPS. Each set of SMUPs will lead to an estimate of MUN. In addition to the mean estimate of MUN, the variance of the estimates is also calculated to describe the variations of the MUN estimates. A smaller variance gives a higher confidence of the robustness of the estimates.

Modifications of The Preferred Embodiments

Thus it will be seen that this invention describes methods and apparatus for estimating motor unit number of a muscle group. A pre-configured electrode array is used to acquire more stable and more certain response waveforms. Based on intermediate waveform processing results, the experimental condition is dynamically adjusted through digitally controlled stimulation and acquisition setup for fast and repeatable motor unit number estimation. An automation algorithm enhances the response waveform quality; determines the optimal solutions for alternation and activation patterns of the response waveforms; derives individual single motor unit potentials; calculates waveform features useful for motor unit number estimation; and reports an estimated value of motor unit number as well as the confidence level of the estimation.

It will be appreciated that still further embodiments of the present invention will be apparent to those skilled in the art in view of the present disclosure. It is to be understood that the present invention is by no means limited to the particular constructions and method steps herein disclosed and/or shown in the drawings, but also comprises any modifications or equivalents within the scope of the invention.

What is claimed is:

1. A method for assessing neuromuscular function by estimating motor unit numbers, the method comprising:
    providing an electrode array for delivering one or more controlled stimuli to a subject using at least one stimulator electrode and for acquiring electric activity signals of one or more motor units of a subject using at least one detector electrode;
    positioning said electrode array on a subject, delivering a stimulus of varying characteristics to the subject and acquiring a set of electric activity signals of one or more motor units of the subject;
    identifying and eliminating any acquired signals due to alternation;
    automatically estimating motor unit number using an automation algorithm,
    wherein the automation algorithm consists of:
        (i) pre-processing acquired responses so as to consolidate and enhance the acquired signals; and
        (ii) identifying plausible new motor unit activation events and corresponding response changes; and
        (iii) determining representatives of single motor unit potential features, and computing approaches; and
        (iv) estimating motor unit number and distribution statistics associated with the motor unit number;
    wherein pre-processing the acquired signals comprises:
        (a) estimating background noise level; and
        (b) determining motor unit activity region in the acquired signal; and
        (c) ordering waveforms according to activity level, and removing noise-only waveforms; and
        (d) identifying and combining waveforms with insignificant morphological variations in relation to background noise;
    wherein a background noise level is determined by:
        (a) using waveform segments known to have no motor unit activity; and
        (b) estimating statistics of noise level, the estimated statistics comprising at least one of mean absolute deviation, standard deviation, and mean square error.

2. A method according to claim 1 wherein the electrode array consists of individual electrodes placed independently on a subject according to anatomical landmarks.

3. A method according to claim 1 wherein the electrode array consists of electrodes whose positions, relative to each other, are fixed for at least some of the electrodes.

4. A method according to claim 1 wherein the electrode array consists of one or more pairs of stimulator electrodes, wherein the relative positions of the stimulator electrodes are selected from the group consisting of: (i) fixed, and (ii) adjustable.

5. A method according to claim 1 wherein the varying characteristics of the stimuli are controlled and adjusted according to one selected from the group consisting of: (i) directly and manually by a user, and (ii) automatically by a computer algorithm.

6. A method according to claim 5 wherein the characteristics of the stimuli include at least one selected from the group consisting of: duration, intensity, polarity, frequency, and other features of electric current to be delivered via stimulus electrodes.

7. A method according to claim 5 wherein the control and adjustment of the stimuli is based on responses acquired from the detector electrodes.

8. A method according to claim 7 wherein responses acquired from the detector electrodes are analyzed for features, wherein the features include at least one selected from the group consisting of: onset, total duration, peak duration, peak amplitude, and peak area.

9. A method according to claim 8 wherein said features also include at least one from the group consisting of: an absolute value of the features, and changes in the absolute value from response to response.

10. A method according to claim 1 wherein an activity-free segment is identified as:
   (a) a segment of waveform acquired with zero or negligible stimulation strength; and/or (b) a segment of waveform occurring before CMAP activity.

11. A method according to claim 1 wherein a motor unit activity region is determined by:
   (a) calculating a median value for all acquired signals; and
   (b) determining a deviation of each individual signal from a calculated median value for each time instance; and
   (c) constructing an activity profile by averaging the deviations over all of the signals; and
   (d) finalizing an activity region by comparing an activity profile with background noise level.

12. A method according to claim 1 wherein waveforms are windowed with the activity region, and windowed waveforms are used for:
   (a) calculating a power level of each waveform within an activity region;
   (b) ordering all waveforms according to the power levels of the waveforms; and
   (c) removing noise-only waveforms if the power level of the waveforms is below a noise threshold.

13. A method according to claim 1 wherein waveform variations are quantified by a similarity measure based on at least one selected from the group consisting of: Euclidian distance, correlation, mean absolute difference, and other comparable measure.

14. A method according to claim 1 wherein waveforms with insignificant morphological variations are:
   (a) identified when e similarity measures of the waveforms are above a threshold value related to noise level; and
   (b) combined to yield a combined waveform by means of at least one selected from the group consisting of: arithmetic averaging, weighted averaging, other linear combination approaches and nonlinear combination approaches.

15. A method according to claim 1 wherein identifying plausible new motor units from a collection of acquired signals comprises:
   (a) optimizing a global search of motor units; and/or
   (b) identifying alternation motor unit responses directly.

16. A method according to claim 15 wherein optimizing a global search of true motor units comprises:
   (a) establishing a ranking criteria for quantitative evaluation of SMUP waveforms at least one of individually, and in groups; and
   (b) establishing a global search strategy to extract SMUPs; and
   (c) extracting SMUPs; and
   (d) optimizing the extracted SMUPs to determine solutions.

17. A method according to claim 16 wherein an SMUP ranking system is established based upon a consideration part of some or all of the features of at least one from the group consisting of: SMUP responses, CMAP responses, response power, response onset, response end, response duration, response turn, response phase, response area, response amplitude, response peaks, and response peak-distance.

18. A method according to claim 16 wherein a SMUP group is defined as one possible combination set of SMUPs extracted from consolidated MU waveforms.

19. A method according to claim 17 wherein an SMUP is scored by:
   (a) calculating an offset of a SMUP waveform power over that of the average level of an SMUP group; and
   (b) calculating an offset of a SMUP waveform onset over that of a CMAP; and
   (c) calculating an offset of a SMUP waveform duration over that of a CMAP; and
   (d) calculating an offset of a SMUP waveform maximum negative peak location over that of a CMAP; and
   (e) calculating an offset of waveform numbers of the SMUP group over a total number of consolidated MU waveforms; and
   (f) weighting, and then summing, all of the offsets so as to generate an SMUP waveform score.

20. A method according to claim 16 wherein a global search strategy is established by:
   (a) determining a decision deferment level; and
   (b) extracting new SMUPs and considering consolidated MU waveforms both with alternation and without alternation issues at a pre-determined deferment level.

21. A method according to claim 20 wherein a decision deferment level is determined as a number that represents a maximum number of alternating MUs, with overlapping thresholds.

22. A method according to claim 21 wherein the decision deferment level is determined so as to be a value between (i) one, which represents step-by-step sequential manual processing, and (ii) a number of total consolidated waveforms, which considers all possible alternation cases in the acquired responses.

23. A method according to claim 20 wherein new SMUPs are extracted at pre-set decision deferment level by:
   (a) considering direct subtraction of sequential consolidated MUs waveforms; and (b) using a MUs waveform to subtract a base waveform; and
   (c) repeating steps (a) and (b) until all the alternation possibilities are exhausted.

24. A method according to claim 23 wherein a base waveform is determined as a consolidated MU waveform based on an alternation consideration at the pre-set decision deferment level.

25. A method according to claim 24 wherein total alternation cases at a pre-set decision deferment level are defined as the power of 2 with an exponent that equals the pre-set decision deferment level −1.

26. A method according to claim 16 wherein SMUPs are optimized by:
   (a) scoring all the SMUP waveforms at least one of individually and in groups;
   (b) identifying a group of SMUPs with highest scores as true SMUPs; and/or
   (c) allowing several alternative solutions to co-exist.

27. A method according to claim 26 wherein several alternative solutions represent solutions with SMUP sets that meet the ranking criteria and have high scores.

28. A method according to claim 15 wherein identifying MU alternation directly comprises:
   (a) searching alternation equations to identify MUs alternation range and avoid direct subtraction of alternating MUs waveforms; and
   (b) extracting potential SMUPs using a combination of IS method and alternation equations; and
   (c) validating potential SMUPs; and
   (d) identifying a SMUPs solution.

29. A method according to claim 28 wherein alternation equations are established by:
   (a) determining a base waveform, from a null signal then first to last consolidated MU waveforms; and
   (b) subtracting the base waveform from all the consolidated MU waveforms at a higher level to obtain residual waveforms; and
   (c) using any combination of residual waveforms to search an identical one in the same residual waveform group (i.e., any identified waveforms satisfying an equation, namely alternation equation).

30. A method according to claim 29 wherein an MU waveform at a higher level represents a consolidated MU waveform that partly or fully has larger features, wherein the features comprise at least one from the group consisting of: power, areas, amplitude, and duration.

31. A method according to claim 29 wherein an identical waveform is measured using a similarity measurement.

32. A method according to claim 28 wherein SMUPs are extracted by:
   (a) identifying alternation equations, if any, until all possibilities are exhausted;
   (b) selecting smaller waveforms from alternation equations as potential SMUPs; or (c) using direct subtraction of sequential MUs waveforms as potential SMUPs, beyond an alternation range in a consolidated MU waveform group.

33. A method according to claim 28 wherein SMUPs are validated by:
   (a) self-checking to identify any MU waveforms that do not satisfy a matching criteria compared with SMUPs' combinations; and
   (b) extracting new SMUPs from MU waveforms that do not satisfy a matching criteria.

34. A method according to claim 33 wherein self-checking uses SMUPs' combinations to compare with consolidated MU waveforms, with criteria being satisfied if a consolidated MU waveform is identical to one SMUPs' combination; otherwise, new information exists in the MU waveforms that do not meet criteria.

35. A method according to claim 33 wherein new SMUPs are extracted from the MU waveforms that do not meet criteria by:
   (a) using an MU waveform to subtract lower level MU waveforms sequentially to obtain extra waveforms; and
   (b) using an obtained extra waveform for self-checking; if the extra waveform in combination with existing potential SMUPs satisfies criteria for two or more MU waveforms, the extra waveform is added to the potential SMUP group.

36. A method according to claim 28 wherein a SMUPs solution is identified by:
   (a) identifying and removing identical waveforms or any composite SMUP waveforms from a potential SMUP group; and
   (b) selecting a set of SMUPs from the potential SMUP group, which has a minimum number of SMUPs, but satisfies all consolidated MUs waveform criteria.

37. A method according to claim 1 wherein representative SMUP features are determined to describe SMUPs' characteristics, which include SMUPs' amplitude and/or areas.

38. A method according to claim 1 wherein computing approaches are determined to calculate sizes of SMUPs features, which include methods of averaging, and/or weighting SMUPs' feature values.

39. A method according to claim 1 wherein motor unit numbers are estimated by using a SMUP representative value divided into a feature value of a maximal CMAP.

40. A method according to claim 1 wherein motor unit number statistics, including motor unit number mean value and standard deviation value, are calculated by using motor unit number estimation alternation solutions.

* * * * *